US00PP24216P2

(12) United States Plant Patent
Butler, III

(10) Patent No.: US PP24,216 P2
(45) Date of Patent: Feb. 4, 2014

(54) ***EPIDENDRUM* PLANT NAMED 'BIG RED'**

(50) Latin Name: *Epidendrum ibaguense*
Varietal Denomination: Big Red

(76) Inventor: George C. Butler, III, Miami, FL (US)

( * ) Notice: Subject to any disclaimer, the term of this patent is extended or adjusted under 35 U.S.C. 154(b) by 93 days.

(21) Appl. No.: 13/385,874

(22) Filed: Mar. 10, 2012

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — C. A. Whealy

(57) ABSTRACT

A new and distinct cultivar of *Epidendrum* plant named 'Big Red', characterized by its upright and columnar plant habit with outwardly arching leaves; freely clumping growth habit; strong stems; freely flowering habit; and dark red-colored flowers.

2 Drawing Sheets

Botanical designation: *Epidendrum ibaguense.*
Cultivar denomination: 'BIG RED'.

BACKGROUND OF THE INVENTION

The present invention relates to a new and distinct cultivar of *Epidendrum* plant, botanically known as *Epidendrum ibaguense* and hereinafter referred to by the name 'Big Red'.

The new *Epidendrum* plant is a naturally-occurring whole plant mutation of *Epidendrum ibaguense* 'Fiesta', not patented. The new *Epidendrum* plant was discovered and selected by the Inventor as a single plant from within a population of plants of 'Fiesta' in a controlled greenhouse environment in Miami, Fla. on Mar. 15, 2010.

Asexual reproduction of the new *Epidendrum* plant by divisions in a controlled environment in Miami, Fla. since Apr. 3, 2010 has shown that the unique features of this new *Epidendrum* plant are stable and reproduced true to type in successive generations of asexual reproduction.

SUMMARY OF THE INVENTION

Plants of the new *Epidendrum* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Big Red'. These characteristics in combination distinguish 'Big Red' as a new and distinct *Epidendrum* plant:

1. Upright and columnar plant habit with outwardly arching leaves.
2. Freely clumping growth habit.
3. Strong stems.
4. Freely flowering habit.
5. Dark red-colored flowers.

Plants of the new *Epidendrum* differ from plants of the parent, 'Fiesta', in the following characteristics:

1. Plants of the new *Epidendrum* are more freely clumping than plants of 'Fiesta'.

2. Plants of the new *Epidendrum* have stronger stems than plants of 'Fiesta'.
3. Plants of the new *Epidendrum* and 'Fiesta' differ in flower color as plants of 'Fiesta' have orange-colored flowers.

Plants of the new *Epidendrum* can also be compared to plants of *Epidendrum* 'Pacific Ember', not patented. In side-by-side comparisons conducted in Miami, Fla., plants of the new *Epidendrum* differed from plants of 'Pacific Ember' in the following characteristics:

1. Plants of the new *Epidendrum* were more freely clumping than plants of 'Pacific Ember'.
2. Plants of the new *Epidendrum* had stronger stems than plants of 'Pacific Ember'.

BRIEF DESCRIPTION OF THE PHOTOGRAPHS

The accompanying photographs illustrate the overall appearance of the new *Epidendrum* plant showing the colors as true as it is reasonably possible to obtain in colored reproductions of this type. Colors in the photographs may differ slightly from the color values cited in the detailed botanical description which accurately describe the colors of the new *Epidendrum* plant.

The photograph on the first sheet is a side perspective view of a typical plant of 'Big Red' grown in a container.

The photograph on the second sheet is a close-up view of a typical inflorescence of 'Big Red'.

DETAILED BOTANICAL DESCRIPTION

The aforementioned photographs and following observations and measurements describe plants grown during the spring in 15-cm containers in a polypropylene-covered shadehouse in Miami, Fla. and under environmental conditions and cultural practices which approximate those generally used in commercial *Epidendrum* production. Plants were one year old when the photographs and the detailed description were taken. In the following description, color references are made to The Royal Horticultural Society Colour Chart, 2007 Edition, except where general terms of ordinary dictionary significance are used.

Botanical classification: *Epidendrum ibaguense* 'Big Red'.

Parentage: Naturally-occurring whole plant mutation of *Epidendrum ibaguense* 'Fiesta', not patented.

Propagation:

*Type*.—By divisions.

*Time to initiate roots*.—About ten days at 27° C. soil temperature.

*Root description*.—Medium in thickness, fleshy; close to 155D in color.

*Rooting habit*.—Dense.

Plant description:

*Plant and growth habit*.—Upright and columnar with outwardly arching leaves; freely clumping habit; vigorous growth habit.

*Plant height* (*soil level to top of foliar plane*).—About 39 cm.

*Plant height* (*soil level to top of inflorescences*).—About 57 cm.

*Plant diameter*.—About 25 cm.

Stem description:

*Length* (*soil level to base of inflorescence*).—About 49 cm.

*Diameter*.—At the base of the plant, about 8 mm to 9 mm; at the base of the inflorescence, about 5 mm.

*Internode length*.—About 1.75 cm.

*Aspect*.—Upright.

*Strength*.—Strong.

*Texture*.—Smooth, glabrous.

*Color*.—Towards the base of the plant, close to 146A faintly tinged with close to 187A; towards the inflorescence, close to 146A heavily tinged with close to 187A.

Foliage description:

*Leaf arrangement*.—Alternate, two-ranked; simple.

*Length, fully expanded*.—About 13 cm.

*Width, fully expanded*.—About 4 cm.

*Shape*.—Lanceolate.

*Apex*.—Acute.

*Base*.—Attenuate.

*Margin*.—Entire.

*Venation*.—Parallel.

*Aspect*.—Outwardly arching, keeled.

*Texture*.—Smooth, glabrous; thick, leathery.

*Color*.—Developing leaves, upper surface: Between N137A and 147A. Developing leaves, lower surface: Close to 146A. Fully expanded leaves, upper surface: Close to N137A to N137C; venation, close to N137A to N137C. Fully expanded leaves, lower surface: Close to 146A; venation, close to 146A.

*Petiole*.—Length: About 3.2 cm. Diameter, flattened: About 2.4 cm. Texture, upper and lower surfaces: Smooth, glabrous; waxy. Color, upper surface: Close to 146B tinged with close to 187A. Color, lower surface: Close to 146A tinged with close to 187A.

Inflorescence description:

*Flower form and arrangement*.—Single star-shaped flowers arranged in dense terminal racemose inflorescences; flowers with two lateral petals, one modified median petal and three sepals that are similar to the lateral petals; freely flowering habit with about 28 flowers developing per flower; flowers face upright to outwardly.

*Fragrance*.—None detected.

*Inflorescence length*.—About 9 cm to 11 cm.

*Inflorescence diameter*.—About 9.5 cm.

*Flower size*.—Length: About 3.1 cm. Diameter: About 3.6 cm. Depth: About 1.6 cm.

*Flower buds*.—Length: About 1.2 cm. Diameter: About 5 mm. Shape: Oblong. Color: Close to 185A to 185B.

*Perianth*.—Lateral petals and sepals: Length: About 1.8 cm Width: About 8 mm. Shape: Lanceolate. Apex: Obtuse to acute. Base: Cuneate, fused into a slender tube. Margin: Entire. Texture, upper and lower surfaces: Smooth, glabrous; velvety. Median petal: Length: Tube, about 2.7 cm; flaring towards the apex into a three-parted palmate platform, about 1.5 cm. Width: Tube, about 3 mm; platform, about 2 cm. Apex: Emarginate. Texture, upper and lower surfaces: Smooth, glabrous, velvety. Color, petals and sepals: When opening and fully opened, upper surface: Close to 53A; throat, mottled with close to 17A and 12A; color does not change with development. When opening and fully opened, lower surface: Close to 182A; tube, close to 144A tinged with close to 182A; color does not change with development.

*Peduncles*.—Length: About 8 cm. Diameter: About 5 mm. Aspect: Upright, erect. Strength: Strong. Texture: Smooth, glabrous. Color: Close to 146A.

*Pedicels*.—Length: About 3.3 cm. Diameter: About 3 mm. Aspect: Outwardly to arching. Strength: Strong, flexible. Texture: Smooth, glabrous. Color: Between 182A and 184B.

*Reproductive organs*.—Stamens: Quantity: One per flower. Anther size: About 1.5 mm by 1 mm. Anther shape: Globular. Anther color: Close to 6A. Pollen amount: Scarce. Pollen color: Close to 6A. Pistils: None observed.

*Seeds and fruits*.—Seed and fruit development have not been observed on plants of the new *Epidendrum*.

Disease & pest resistance: Plants of the new *Epidendrum* have not been observed to be resistant to pathogens or pests common to *Epidendrum*.

It is claimed:

1. A new and distinct *Epidendrum* plant named 'Big Red' as illustrated and described.

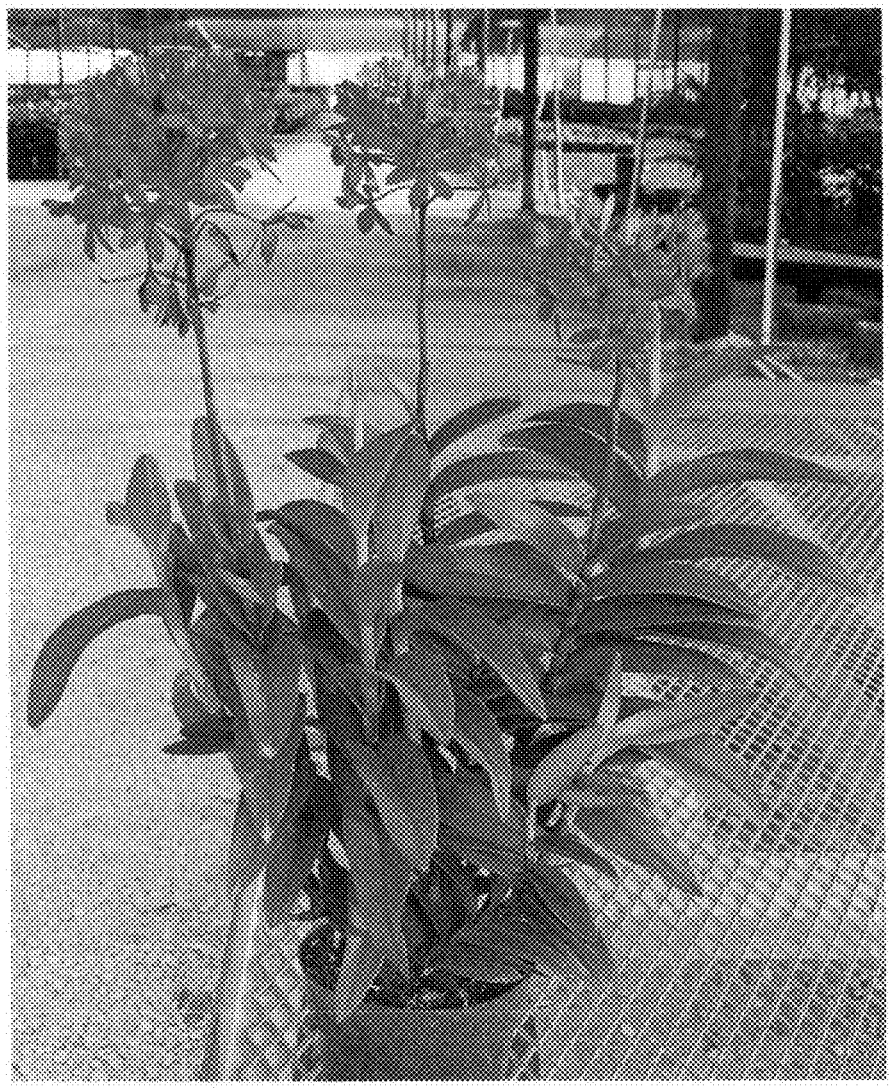

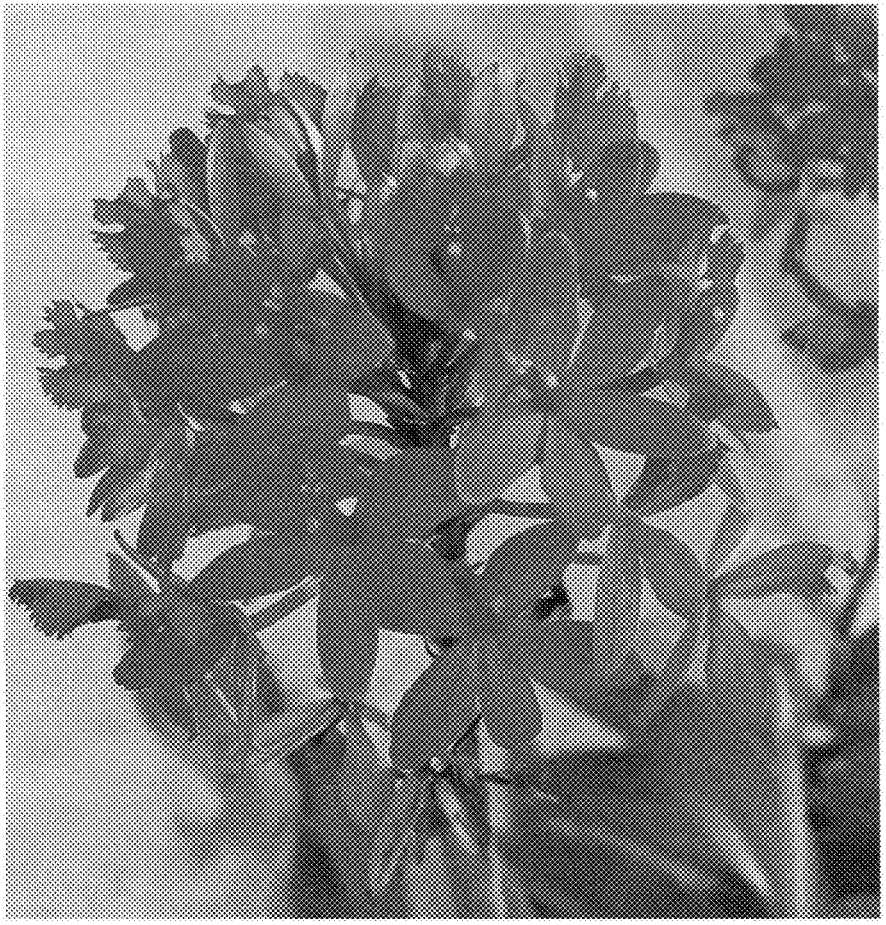

* * * * *